United States Patent [19]
Horie et al.

[11] Patent Number: 5,422,703
[45] Date of Patent: Jun. 6, 1995

[54] REFLECTED LIGHT MEASURING METHOD AND REFLECTED LIGHT MEASURING APPARATUS FOR A MICROSCOPIC PHOTOMETRIC SYSTEM

[75] Inventors: Masahiro Horie; Nariaki Fujiwara; Masahiko Kokubo, all of Kyoto, Japan

[73] Assignee: Dainippon Screen Mfg. Co., Ltd., Kyoto, Japan

[21] Appl. No.: 262,619

[22] Filed: Jun. 20, 1994

[30] Foreign Application Priority Data

Jun. 21, 1993 [JP] Japan ................................ 5-174761

[51] Int. Cl.6 ................................................ G01B 11/00
[52] U.S. Cl. ........................................ 356/445; 356/382
[58] Field of Search .......................... 356/445, 448, 382

[56] References Cited

U.S. PATENT DOCUMENTS

| | | | |
|---|---|---|---|
| 4,566,798 | 1/1986 | Hass | 356/448 |
| 5,108,176 | 4/1992 | Malin et al. | 356/243 |
| 5,233,405 | 8/1993 | Wildnauer et al. | 356/328 |

*Primary Examiner*—Richard A. Rosenberger
*Attorney, Agent, or Firm*—Ostrolenk, Faber, Gerb & Soffen

[57] ABSTRACT

A method of measuring light reflected by a test sample with a microscopic photometric system. The test sample placed in an in-focus position of an objective is irradiated, and light reflected by the test sample is measured. Stray light generated by microscopic optics including the objective is measured with the test sample placed in an out-of-focus position of the objective. Light actually reflected by the test sample is determined from a difference between the reflected light and the stray light measured.

11 Claims, 5 Drawing Sheets

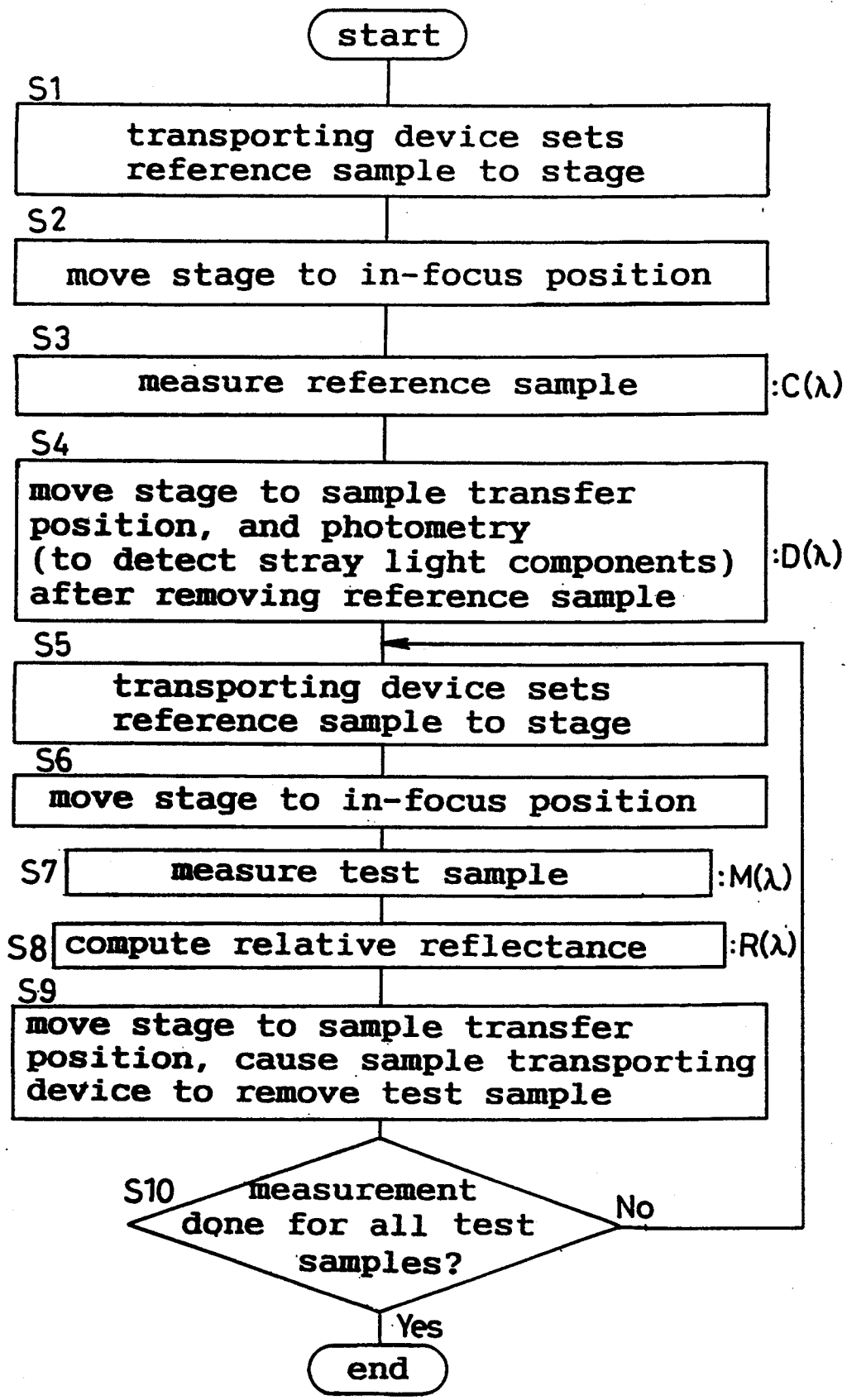

REFLECTED LIGHT MEASURING METHOD AND REFLECTED LIGHT MEASURING APPARATUS FOR A MICROSCOPIC PHOTOMETRIC SYSTEM

BACKGROUND OF THE INVENTION (1) Field of the Invention

The present invention relates to a microscopic photometric system for use in film thickness measurement, line width measurement or the like. More particularly, the invention relates to a method executed with use of such a microscopic photometric system to measure light reflected by minute test samples, and to a reflected light measuring apparatus.

(2) Description of the Related Art

At a testing stage of a semiconductor manufacturing process, for example, a thickness of silicon oxide film formed on a silicon substrate is measured by first measuring light reflected by a surface of the substrate.

A conventional apparatus used for measuring this reflected light will be described hereinafter in relation to a relative reflectance measuring apparatus.

In this apparatus, light from a light source such as a halogen lamp, deuterium lamp or the like is reflected toward a sample by a half mirror mounted in the body tube of a microscope, and projected through an objective to a surface of the sample. Light reflected by the sample surface and having a predetermined wavelength range travels through the objective and the half mirror to a spectrophotometric unit. This spectrophotometric unit has an electromagnetic shutter disposed at an entrance thereof to open and close the entrance, and a pinhole disposed downstream of the shutter. The light having passed through the pinhole is dispersed by a concave diffraction grating and reaches a one-dimensional solid-state image pickup device. This image pickup device has a signal output connected to a CPU included in a data processor. The CPU also controls opening and closing of the electromagnetic shutter mentioned above.

Methods of measuring a relative reflectance with this apparatus will be described next.

In a first method, a sample to be used as a reference (a silicon substrate without silicon oxide film in this example) is placed on the stage of the microscope first of all. Intensity $C(\lambda)$ of light reflected by the sample and incident upon the spectrophotometric unit is measured.

Next, the electromagnetic shutter at the entrance is closed to darken the spectrophotometric unit. Then, a dark current $D(\lambda)$ of the one-dimensional solidstate image pickup device is measured.

A sample to be tested for relative reflectance (a silicon substrate having silicon oxide film in this example) is placed on the stage of the microscope next. Intensity $M(\lambda)$ of light reflected by this test sample is measured after opening the electromagnetic shutter of the spectrophotometric unit.

Based on the above measurements, relative reflectance $R(\lambda)$ is derived from the following equation:

$$R(\lambda) = \{M(\lambda) - D(\lambda)\} / \{C(\lambda) - D(\lambda)\} \quad (1)$$

In a second method, a sample to be used as a reference (a silicon substrate without silicon oxide film in this example) is placed on the stage of the microscope first of all. Intensity $C(\lambda)$ of light reflected by the sample and incident upon the spectrophotometric unit is measured.

Next, a perfect diffuser plate or the like having a minimal reflectance which may be regarded as 0% is placed on the stage, and light intensity $D(\lambda)$ is measured.

Then, as in the first method, light intensity $M(\lambda)$ from a test sample is measured. In this method also, relative reflectance $R(\lambda)$ is derived from equation (1) above.

The conventional methods described above have the following drawbacks.

In the first method, the dark current of the one-dimensional solid-state image pickup device may be eliminated from light intensities M and C in the above equation (1). However, it is impossible to eliminate stray light (i.e. undesirable light due to causes other than normal refraction or reflection) occurring between the electromagnetic shutter of the spectrophotometric unit and the interior of the microscope body tube and between the objective and the sample. The stray light lowers the precision of relative reflectance measurement.

This problem will particularly be described with reference to FIG. 1.

FIG. 1 is a graph showing relative reflectance $R(\lambda)$ obtained from the first method above, and relative reflectance $T(\lambda)$ obtained theoretically. The theoretical relative reflectance $T(\lambda)$ is derived from a film thickness on the test sample, refractive index of the film, absorption coefficient of the film, refractive index of the substrate, absorption coefficient of the substrate, and so on.

As seen from this graph, the relative reflectance $R(\lambda)$ influenced by the stray light and the theoretical relative reflectance $T(\lambda)$ are significantly different in minimal regions.

Such stray light is generated chiefly as a result of the light from the light source scattering when passing through the half mirror in the body tube of the microscope, or reflected by the incident surface of the objective to enter the spectrophotometric unit directly instead of traveling by way of the sample. Particularly where the objective comprises a reflecting objective formed of a plurality of concave or convex reflecting mirrors, light incident on the optical axis of the reflecting objective is subjected to regular reflection to enter the spectrophotometric unit directly. This results in increased influences of the stray light.

The drawback may be mitigated to some extent by applying tufty paper (flockpaper) on inner walls of the body tube of the microscope to scatter light, or by forming recesses (light traps) in axial portions of spherical reflecting mirrors of the reflecting objective to scatter light. However, these provisions cannot remedy the drawback completely.

The second method can remove some of the influences of stray light since the intensity D of light reflected by the perfect diffuser plate corrects reflected light intensities M and C. However, the stray light cannot be removed completely since no perfect diffuser plate has 0% reflectance over a wide range of wavelengths. A complex corrective computation of reflectance would be required to improve the precision of measurement by this method.

Where a light source for emitting ultraviolet light is used, the perfect diffuser plate will deteriorate due to ultraviolet light. It will be extremely difficult to optically maintain 0% reflectance.

SUMMARY OF THE INVENTION

The present invention has been made having regard to the state of the art noted above, and its object is to provide a reflected light measuring method and a reflected light measuring apparatus for use with a microscopic photometric system, which are capable of accurately measuring reflected light by excluding stray light generated in the interior of the body tube of a microscope without using a perfect diffuser plate or the like.

The above object is fulfilled, according to the present invention, by a method of measuring light reflected by a test sample with a microscopic photometric system, comprising the steps of:

irradiating the test sample placed in an in-focus position of an objective, and measuring light reflected by the test sample;

measuring stray light generated by microscopic optics including the objective, with the test sample placed in an out-of-focus position of the objective; and determining light actually reflected by the test sample from a difference between the reflected light and the stray light measured at the above steps.

When the test sample placed in the out-of-focus position of the objective is irradiated through the objective, light reflected by the test sample does not enter the objective. Thus, a light intensity measured in this condition represents stray light components generated by the microscopic optics. It is therefore possible to determine light actually reflected by the test sample, free from the stray light components, by subtracting the above light intensity (stray light components) from the light intensity measured when the test sample is placed in the in-focus position of the objective.

The stray light can be measured after moving a stage supporting the test sample, away from the objective along an optical axis of the objective, to place the test sample in the out-of-focus position of the objective. Consequently, the stray light measuring step is executed with facility, with the out-of-focus position attained by moving the stage away along the optical axis of the objective.

Alternatively, the stray light can be measured after removing the test sample from a stage defining an opening in a portion thereof corresponding to the optical axis of the objective. When light is emitted through the objective after the test sample is removed from the stage, the light passes through the opening of the stage without being reflected to the objective. Thus, the stray light may be measured by removing the test sample from the stage.

Preferably, the out-of-focus position is spaced from the in-focus position by at least 100 times a focal depth of the objective.

Where the out-of-focus position is at least 100 times the focal depth of the reflecting objective, the reflected light entering the objective in the out-of-focus condition is about 0.1% of the reflected light in the in-focus condition. This allows a measurement of stray light components to be effected with high precision in a further aspect of the present invention, there is provided an apparatus for measuring light reflected by a test sample, comprising:

a light source for emitting illuminating light to the test sample;

photometric means for outputting a light intensity signal representing an intensity level of incident light;

microscopic optics having an objective for receiving light from an in-focus position of the objective, the microscopic optics inputting the light to the photometric means;

a stage disposed on an optical axis of the microscopic optics for supporting the test sample, the stage being movable along the optical axis;

control means for selectively placing the test sample in the in-focus position and an out-of-focus position of the objective; and reflected light computing means for receiving a first light intensity signal outputted from the photometric means when the test sample is placed in the in-focus position and a second light intensity signal outputted from the photometric means when the test sample is placed in the out-of-focus position, and for subtracting the second light intensity signal from the first light intensity signal, thereby outputting a difference signal as intensity of light reflected from the test sample.

The reflected light computing means subtracts the second light intensity signal outputted from the photometric means when the test sample is placed in the out-of-focus position by the control means, from the first light intensity signal outputted from the photometric means when the test sample is placed in the in-focus position by the control means. That is, the stray light components are subtracted to determine with high precision light actually reflected by the test sample.

The control means may, for example, comprise:

first control means for placing the test sample in the in-focus position based on an amount of displacement of the test sample with respect to a focal point of the objective; and second control means for placing the test sample in a predetermined out-of-focus position.

With this construction, the first control means places the test sample in the in-focus position of the objective based on an amount of displacement. Thus, the test sample can be placed in the in-focus position accurately.

The stage may define an opening in a portion thereof intersecting the optical axis, the second control means comprising sample transport means for transporting the test sample to and from the stage.

With this construction, after the sample transport means removes the test sample from the stage, light emerging from the objective passes through the opening of the stage, thereby enabling a stray light measurement. This realizes an efficient measurement.

The apparatus according to the present invention may further comprise reflectance computing means for receiving an object reflected light intensity signal obtained for an object test sample and a reference reflected light intensity signal obtained for a reference test sample, and for determining a reflectance of the object test sample relative to the reference test sample by dividing the object reflected light intensity signal by the reference reflected light intensity signal.

This construction is capable of accurately measuring a reflectance of the object test sample relative to the reference test sample.

Preferably, the objective comprises a reflecting objective.

With a refracting objective, it is difficult to secure the same focal length over a wide range of wavelengths.

However, a reflecting objective maintains substantially the same focal length over a wide range wavelengths. Thus, measurement can be made of reflected light over a wide wavelength range.

BRIEF DESCRIPTION OF THE DRAWINGS

For the purpose of illustrating the invention, there are shown in the drawings several forms which are presently preferred, it being understood, however, that the invention is not limited to the precise arrangements and instrumentalities shown.

FIG. 6 is a flowchart showing a measuring sequence of the system in the second embodiment.

DETAILED DESCRIPTION OF THE PREFERRED EMBODIMENTS

Preferred embodiments of the present invention will be described in detail hereinafter with reference to the drawings.

First Embodiment

Figure 2:
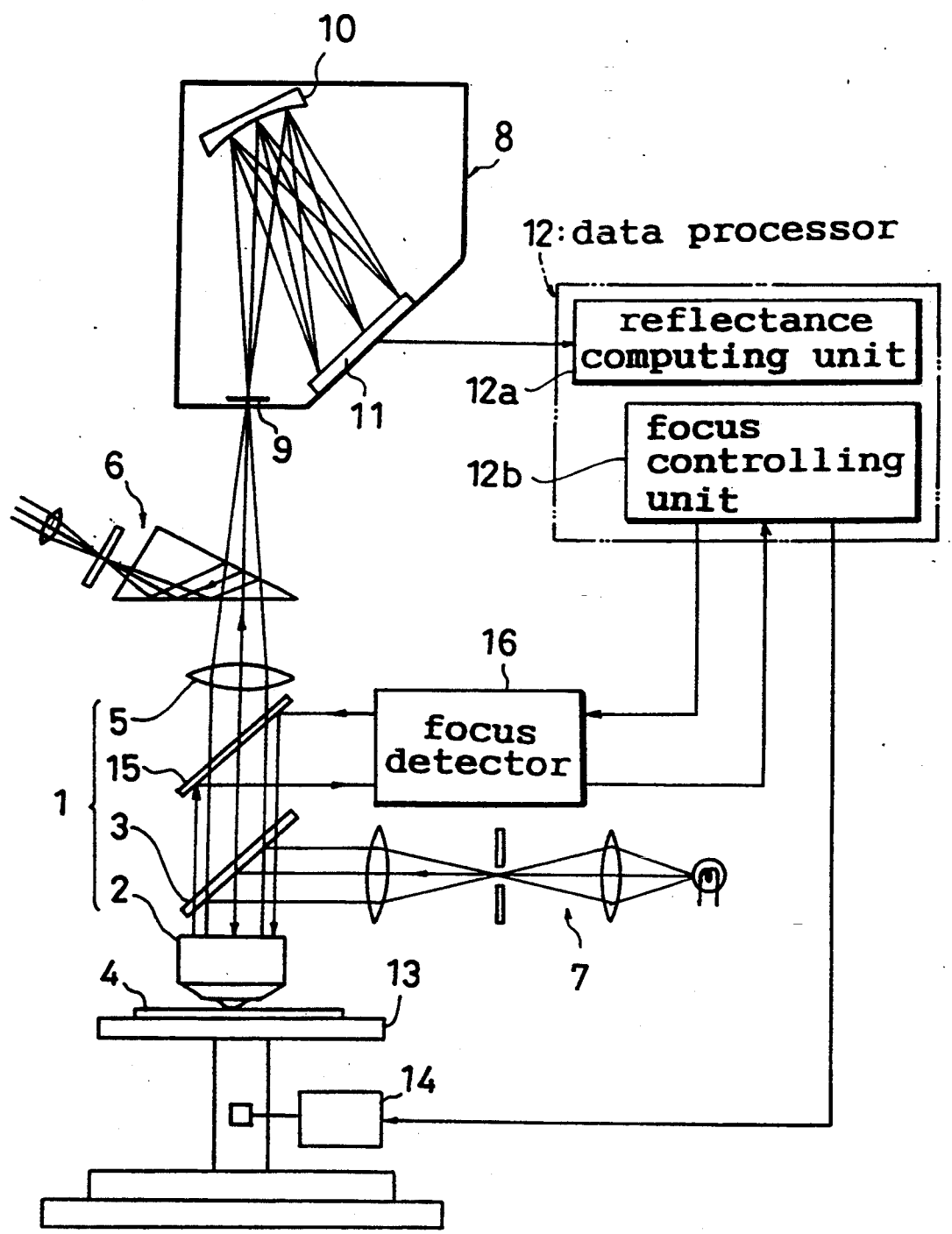
FIG. 2 is a schematic view of a microscopic photometric system in a first embodiment of the present invention.

FIG. 2 is a schematic view of a microscopic photometric system used in the method according to the present invention.

Microscopic optics 1 include a reflecting objective 2, a half mirror 3 for reflecting light from a light source described later toward the reflecting objective 2, a condenser lens 5 for condensing light reflected by a test sample 4, and a half mirror 15. An eyepiece section 6 is disposed above the condenser lens 5 for taking out part of condensed light. A light source 7 is disposed laterally of the half mirror 3. The light source 7 is composed of a halogen lamp for emitting light of 400 to 1000 nm wavelengths including infrared light, a deuterium lamp for emitting light of 200 to 400 nm wavelengths including ultraviolet light, illuminating lenses and so on. A focus detector 16 includes a semiconductor laser, an optical position detecting element and so on. The focus detector 16 is operable in response to a command from a data processor 12 to detect a displacement of the sample 4 relative to an in-focus position of the reflecting objective 2, and transmit displacement information to the data processor 12. The microscopic optics 1, eyepiece section 6, light source 7 and focus detector 16 are mounted in the body tube of a microscope not shown.

A spectrophotometric unit 8 is disposed above the eyepiece section 6 for detecting a spectral intensity of reflected light. The spectrophotometric unit 8 includes a pinhole plate 9 defining a pinhole and disposed at a light entrance in a lower position thereof. The spectrophotometric unit 8 further includes a concave diffraction grating 10 for breaking up reflected light into a spectrum of one wavelength. The light broken into the spectrum by the concave diffraction grating 10 forms an image on a surface of a CCD (Charge Coupled Device) 11 acting as a one-dimensional solid-state image pickup device. The CCD 11 may be replaced with a PDA (Photo Diode Array). The electromagnetic shutter employed in the conventional system is omitted from the system according to the present invention.

The CCD 11 converts light intensity into an electric signal and transmits it to a reflectance computing unit 12a of the data processor 12. The reflectance computing unit 12a has a function to compute a relative reflectance, which will be described hereinafter, from the signal received from the spectrophotometric unit 8. The data processor 12 also includes a focus control unit 12b having a function to drive a pulse motor 14 based on the displacement information received from the focus detector 16, thereby to vertically move the stage 13 supporting the test sample 4, as appropriate, for placing the sample 4 in the in-focus position of the reflecting objective 2, and a function to place the sample 4 in an out-of-focus position of the reflecting objective 2.

Figure 3:
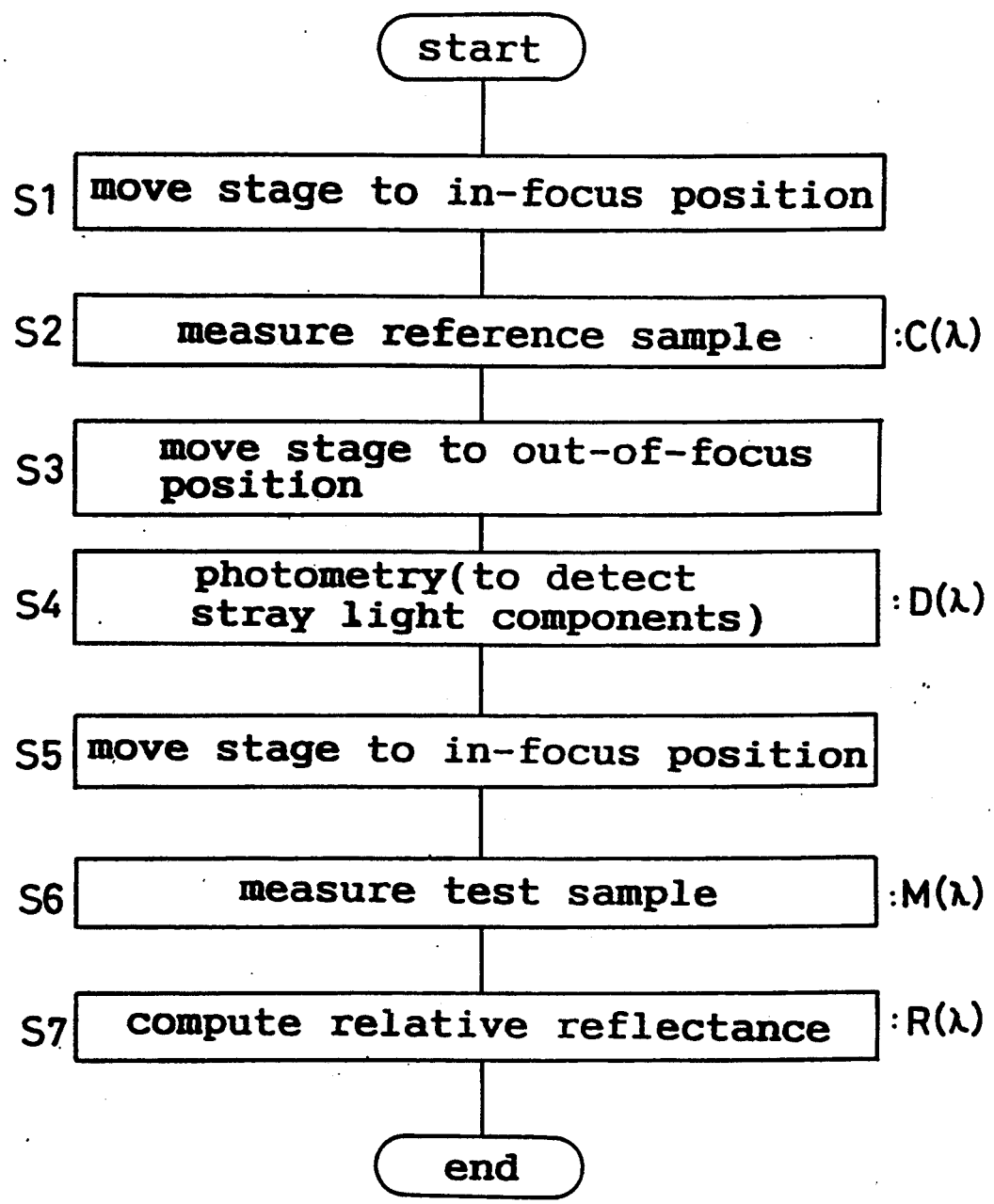
FIG. 3 is a flowchart showing a measuring sequence of the system in the first embodiment.
Figure 4:
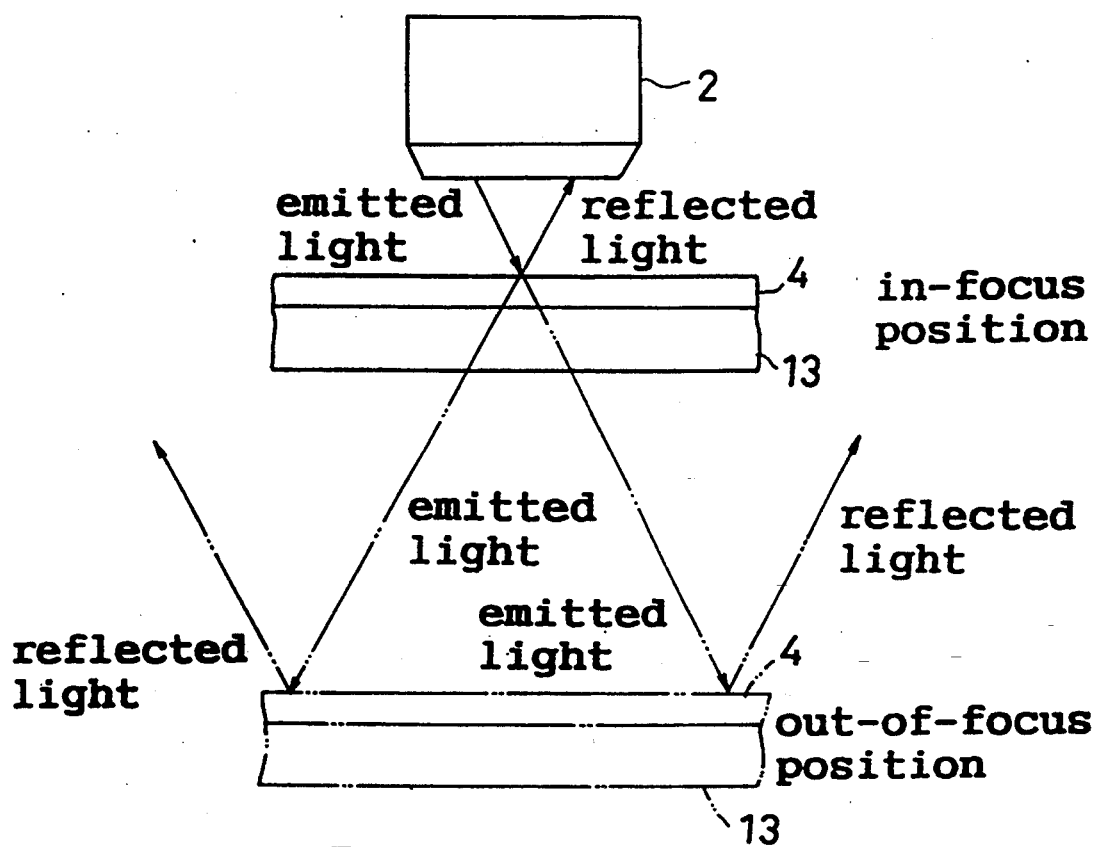
FIG. 4 is an explanatory view of functions of the system in the first embodiment.

A method of measuring relative reflectance with this system will be described next with reference to the flowchart of FIG. 3 showing a sequence of measurement and to the explanatory view of FIG. 4 showing the in-focus position and out-of-focus position. By way of example, this method is directed to a measurement of reflectance relative to a silicon substrate of silicon oxide film formed on the silicon substrate.

First, measurement is made of light reflected from a sample (reference sample), e.g. a silicon substrate with no silicon oxide film, providing a reference for the relative reflectance of the test sample 4. The operator places this reference sample on the stage 13. The focus control unit 12b drives the pulse motor 14, based on the displacement information from the focus detector 16, to move the stage 13 so that the reference sample is located in the in-focus position of the reflecting objective 2 (step S1). As shown in FIG. 4, light emerging from the reflecting objective 2 is reflected by a surface of the reference sample in the in-focus position. The reflected light is transmitted through the microscopic optics 1 to the spectrophotometric unit 8, whereby reflected light intensity $C(\lambda)$ is measured (step S2). This reflected light intensity $C(\lambda)$ includes stray light components generated within the microscopic optics 1.

Next, the focus control unit 12b drives the pulse motor 14 based on the displacement information from the focus detector 16, to move the stage 13 away from the reflecting objective 2 to place the reference sample in a position (hereinafter called the out-of-focus position) sufficiently spaced from the in-focus position of the reflecting objective 2 (step S3). In this embodiment, the stage 13 is lowered by 10 mm. Light radiating from the reflecting objective 2 to the reference sample in the out-of-focus position is reflected by the reference sample surface such that almost all of the light travels outwardly of the microscopic photometric system without returning to the reflecting objective 2 (see the out-of-focus position in FIG. 4).

Preferably, the out-of-focus position is at least 100 times the focal depth of the reflecting objective 2. With such setting, the reflected light entering the reflecting objective 2 at this time is about 0.1% of the reflected light in the in-focus condition. This allows a measurement of stray light components to be effected with high precision.

In this condition, reflected light intensity $D(\lambda)$ is measured (step S4). This value represents stray light generated within the microscopic optics 1 and dark current of the CCD 11.

Next, the operator removes the reference sample from the stage 13, and places a sample to be tested for relative reflectance on the stage 13 as test sample 4 which is, for example, a silicon substrate having silicon oxide film formed thereon (i.e. an object sample).

As at step S1, the stage 13 supporting the object sample is moved to the in-focus position (step S5). Then, intensity $M(\lambda)$ of light reflected by the object sample is measured (step S6).

Based on the three measurements, i.e. reflected light intensity $C(\lambda)$ of the reference sample, reflected light intensity $D(\lambda)$ influenced by stray light, and reflected light intensity $M(\lambda)$ of the object sample, the reflectance computing unit 12a derives relative reflectance $R(\lambda)$ from the equation (1) (step S7).

In this embodiment, stray light is measured by moving the stage 13 supporting the reference sample to the out-of-focus position and obtaining reflected light intensity $D(\lambda)$. This step may be executed by using the object sample. Further, the stray light measurement may be carried out by moving the unloaded stage 13 to the out-of-focus position and obtaining reflected light $D(\lambda)$.

Second Embodiment

In the first embodiment, reflected light intensity $D(\lambda)$ including stray light components is measured by moving the stage 13 to place the sample 4 in the out-of-focus position. The present invention is not limited to such measurement. A different mode of measurement will be described hereinafter with reference to FIG. 5.

Figure 5:
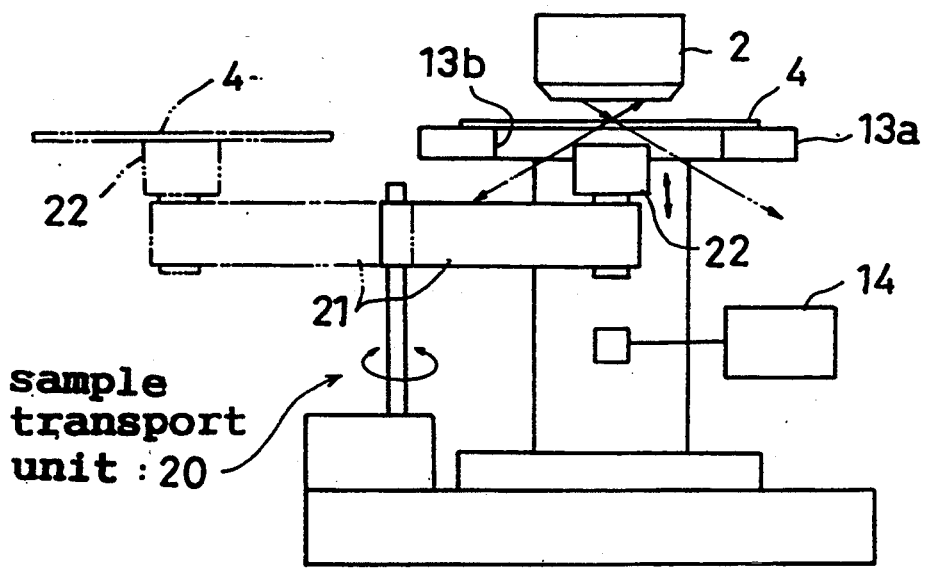
FIG. 5 is a schematic view of a principal portion of a microscopic photometric system in a second embodiment of the present invention.

FIG. 5 is a schematic view of a portion below the reflecting objective 2 of the microscopic photometric system in the first embodiment. In FIG. 5, like reference numerals are used to identify like parts in the first embodiment shown in FIG. 2. Numeral 20 denotes a sample transporting device for automatically changing test samples 4, which includes a pivot arm 21 supported by a rotatable support, and a sample suction unit 22. The sample transporting device 20 transports a sample 4 and places it on a stage 13a defining a U-shaped opening 13b centrally thereof. At this time, the stage 13a is moved by the pulse motor 14 from the in-focus position to a sample transfer position. The sample transfer position is a position of the stage 13a sufficiently spaced from a lower end of the reflecting objective 2 for allowing the sample transporting device 20 to transport the sample 4 to/from the stage 13a.

A method of measuring relative reflectance with this system will be described next with reference to the flowchart of FIG. 6 showing a sequence of measurement.

First, the sample transporting device 20 places a silicon substrate providing a reference for relative reflectance (reference sample) on the stage 13a in the sample transfer position (step S1). The pivot arm 21 having transported the reference sample is retracted from the vicinity of the stage 13a. The focus control unit 12b drives the pulse motor 14, based on the displacement information from the focus detector 16, to move the stage 13a so that the reference sample is located in the in-focus position of the reflecting objective 2 (step S2). Then, reflected light intensity $C(\lambda)$ is measured of the reference sample lying in the in-focus position (step S3).

Next, the focus control unit 12b drives the pulse motor 14 based on the displacement information from the focus detector 16, to move the stage 13a to the sample transfer position. Then, the sample transporting device 20 removes the reference sample from the stage 13a, whereupon reflected light intensity $D(\lambda)$ is measured (step S4). In this embodiment, reflected light intensity $D(\lambda)$ including stray light components is measured while the pivot arm 21 of the sample transporting device 20 is making a pivotal movement to transport the sample 4 from the stage 13a. That is, since the stage 13a has the central opening 13b, light radiating from the reflecting objective 2 passes through this opening 13b, with no reflected light entering the reflecting objective 2.

The sample transporting device 20 places on the stage 13a a silicon substrate having silicon oxide film formed thereon (i.e. an object sample). Then, the stage 13a is moved to the in-focus position based on the displacement information from the focus detector 16 (step S6). Intensity $M(\lambda)$ of light reflected by the object sample in the in-focus position is measured (step S7).

Based on the three measurements, the reflectance computing unit 12a derives relative reflectance $R(\lambda)$ from the equation (1) (step S8).

The stage 13a is moved to the sample transfer position, and the object sample is removed from the stage 13a by the sample transporting device 20 (step S9). The data processor 12 checks whether measurement has been completed for all test samples (step S10). If one or more test samples remain to be measured, the operation returns to step S5 to repeat the subsequent steps until all the test samples are measured.

In this embodiment, as described above, the out-of-focus condition is attained during transport of a sample, to carry out the relative reflectance measurement efficiently. This feature provides a great advantage particularly with an automatic measuring apparatus for automatically changing and successively measuring numerous test samples.

In the above method, the measurement of stray light components is made only once (step S4), and thereafter levels of reflected light intensity are measured for a plurality of test samples successively (step S7) without measuring stray light components. Instead, stray light components may be measured prior to the reflected light intensity measurement for each successive test sample. This will positively eliminate the influences of stray light.

The precision of relative reflectance $R(\lambda)$ obtained by the foregoing methods will be described next with reference to FIG. 7.

Figure 7:
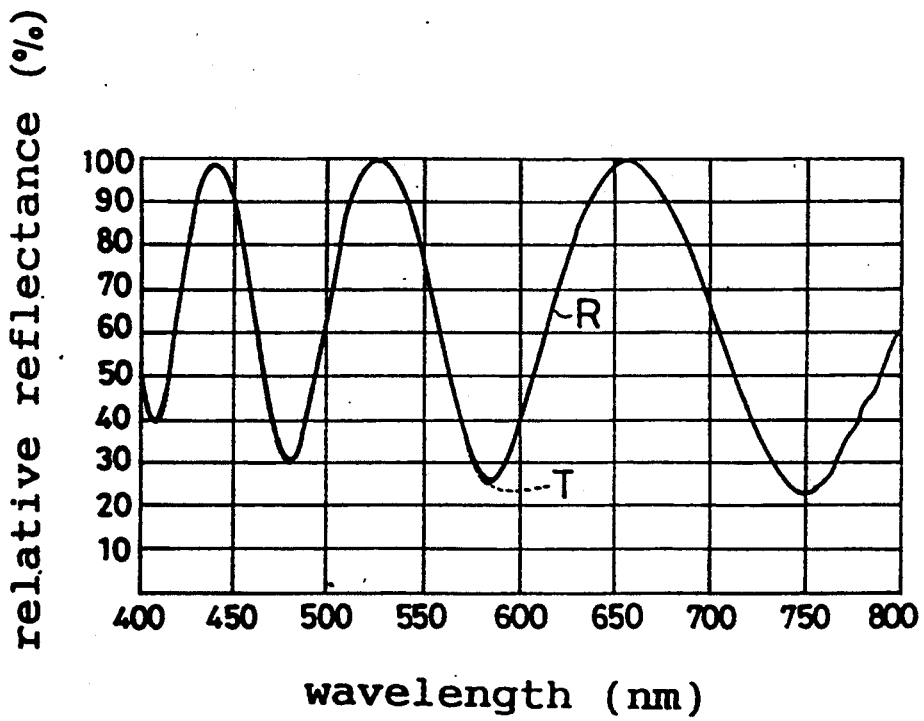
FIG. 7 is a graph showing a relative reflectance measured by the systems of the present invention and a theoretical relative reflectance.

FIG. 7 is a graph showing relative reflectance $R(\lambda)$ obtained by the methods according to the present invention, and relative reflectance $T(\lambda)$ obtained theoretically. As noted in the description of the prior art, the theoretical relative reflectance $T(\lambda)$ is derived from a film thickness on the test sample, refractive index of the film, and so on.

Figure 1:
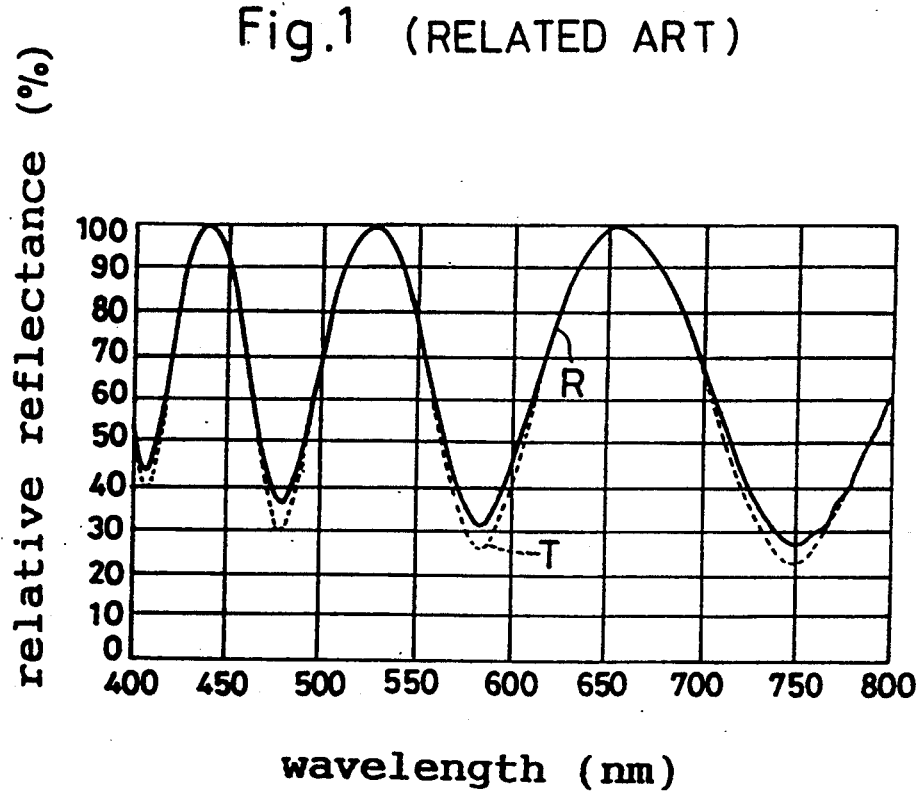
FIG. 1 is a graph showing a relative reflectance measured by a conventional method and a theoretical relative reflectance.

As seen from this graph, the relative reflectance $R(\lambda)$ and the theoretical relative reflectance $T(\lambda)$ are coincidental even in minimal regions, in contrast with the prior art example (see FIG. 1).

The foregoing embodiments have been described, taking the methods of measuring relative reflectance with a microscopic photometric system. The present invention is not limited thereto, but may be applied to various other systems or apparatus such as film thickness measuring apparatus and line width measuring apparatus utilizing reflected light.

The present invention may be embodied in other specific forms without departing from the spirit or essential attributes thereof and, accordingly, reference should be made to the appended claims, rather than to the foregoing specification, as indicating the scope of the invention.

What is claimed is:

1. A method of measuring light reflected by a test sample with a microscopic photometric system, comprising the steps of:

irradiating said test sample placed in an in-focus position of an objective, and measuring light reflected by said test sample;

measuring stray light generated by microscopic optics including said objective, with said test sample placed in an out-of-focus position of said objective; and determining light actually reflected by said test sample from a difference between said reflected light and said stray light measured at the above steps.

2. A method as defined in claim 1, wherein said stray light is measured after moving a stage supporting said test sample, away from said objective along an optical axis of said objective, to place said test sample in said out-of-focus position of said objective.

3. A method as defined in claim 2, wherein said out-of-focus position is spaced from said in-focus position by at least 100 times a focal depth of said objective.

4. A method as defined in claim 1, wherein said stray light is measured after removing said test sample from a stage defining an opening in a portion thereof corresponding to an optical axis of said objective.

5. An apparatus for measuring light reflected by a test sample, comprising: a light source for emitting illuminating light to said test sample;

photometric means for outputting a light intensity signal representing an intensity level of incident light;

microscopic optics having an objective for receiving light from an in-focus position of said objective, said microscopic optics inputting said light to said photometric means;

a stage disposed on an optical axis of said microscopic optics for supporting said test sample, said stage being movable along said optical axis;

control means for selectively placing said test sample in said in-focus position and an out-of-focus position of said objective; and reflected light computing means for receiving a first light intensity signal outputted from said photometric means when said test sample is placed in said in-focus position and a second light intensity signal outputted from said photometric means when said test sample is placed in said out-of-focus position, and for subtracting said second light intensity signal from said first light intensity signal, thereby outputting a difference signal as intensity of light reflected from said test sample.

6. An apparatus as defined in claim 5, wherein said control means comprises:

first control means for placing said test sample in said in-focus position based on an amount of displacement of said test sample with respect to a focal point of said objective; and second control means for placing said test sample in a predetermined out-of-focus position.

7. An apparatus as defined in claim 6, wherein said first control means comprises;

focus detecting means for outputting a displacement signal representing said amount of displacement;

drive means for moving said stage along said optical axis; and focusing control means for controlling said drive means based on said displacement signal.

8. An apparatus as defined in claim 7, wherein said second control means comprises defocusing control means for controlling said drive means based on a predetermined out-of-focus position signal.

9. An apparatus as defined in claim 7, wherein said stage defines an opening in a portion thereof intersecting said optical axis, said second control means comprising sample transport means for transporting said test sample to and from said stage.

10. An apparatus as defined in claim 5, further comprising reflectance computing means for receiving an object reflected light intensity signal obtained for an object test sample and a reference reflected light intensity signal obtained for a reference test sample, and for determining reflectance of said object test sample relative to said reference test sample by dividing said object reflected light intensity signal by said reference reflected light intensity signal.

11. An apparatus as defined in claim 5, wherein said objective comprises a reflecting objective.

* * * * *